United States Patent [19]
Schneider et al.

[11] Patent Number: 5,545,671
[45] Date of Patent: Aug. 13, 1996

[54] ANTIMETASTICALLY ACTING AGENTS

[75] Inventors: Martin Schneider; Ekkehard Schillinger, both of Berlin, Germany

[73] Assignee: Schering Aktiengesellschaft, Berlin, Germany

[21] Appl. No.: 234,515

[22] Filed: Apr. 28, 1994

Related U.S. Application Data

[63] Continuation of Ser. No. 856,161, Apr. 2, 1992, abandoned.

[30] Foreign Application Priority Data

Oct. 5, 1989 [DE] Germany .......................... 39 33 523.2

[51] Int. Cl.⁶ .......................... A61K 31/19; A61K 31/557
[52] U.S. Cl. ................................................. 514/573
[58] Field of Search ............................................... 514/573

[56] References Cited

PUBLICATIONS

Advances in Prostaglandin, Thromboxane; and Leukotriene Research, vol. 21B, prostaglandins and Related Compounds, Seventh International Conference, Florence, Italy, 1990, pp. 913–916, Giraldi et al., "Antimetastatic action of stable prostacyclin analogs in mice".

Advances in Prostaglandin Thromboxane, and Leukotriene Research, vol. 21B Prostaglandins and Related Compounds, Seventh International Conference, Florence, Italy, 1990, pp. 901–908, Schneider et al., "Effects of prostacyclin analogues in in vivo tumor models".

European Search Report of Feb. 19, 1992 for Appln. No. EP 90 25 0257.

Communication in Intenatinal PCT Appln. PCT/EP 90/01676; International Filing Date: Oct. 5, 1990.

*Primary Examiner*—Jerome D. Goldberg
*Attorney, Agent, or Firm*—Millen, White, Zelano, & Branigan, P.C.

[57] ABSTRACT

The invention relates to an antimetastatically acting agent consisting of Eptaloprost, Cicaprost or combinations of $TXA_2$ antagonist and prostacyclin derivatives.

9 Claims, 5 Drawing Sheets

ANTIMETASTICALLY ACTING AGENTS

This application is a continuation, of application Ser. No. 07/856,161, filed Apr. 2, 1992 now abandoned.

BACKGROUND OF THE INVENTION

This invention relates to a new agent with antimetastatic action.

After application of prostacyclin ($PGI_2$) in high dosage (10 mg/kg) shortly before intravenous injection of tumor cells of B16 mouse melanoma, K. V. Honn et al. [Science 212, 1270 (1981)] observed a reduction of the number of lung metastases. This action is ascribed to an inhibition of the tumor cell adhesion and aggregation. But for an application the half-life is too short and the dose of $PGI_2$ is too high. Therefore, with the more stable prostacylin analog, Iloprost, a pharmaceutical application would be more conceivable.

V. costantini et al. (Cancer Chemother. Pharmacol. 22, 289 (1988) compared the antimetastatic action of $PGI_2$ (5 and 10 mg/kg) and Iloprost (0.1 and 0.2 mg/kg) on the formation of lung metastases of the melanoma cell line BLG after intravenous injection of the tumor cells in mice. The action was a function of the number of applied tumor cells and the periods between substance and tumor cell application. In various test arrangements, Iloprost proved to be clearly superior to $PGI_2$ from the dose, the duration of action and the achieved inhibition action.

Piccini et al. (1988) obtained comparable data on the Lewis lung carcinoma of the mouse by use of the same dosages and similar test arrangements. In a one-time dose of 0.2 mg/kg, 1 hour before injection of the tumor cells, Iloprost reduced the number of lung metastases by more than 90%.

But test arrangements such as intravenous injection of tumor cells or one-time substance administration clinically have little relevance.

Another test described by Piccini et al. is more meaningful. In a standard model for establishing an antimetastatic potency, namely i.m. implantation of a primary tumor (Lewis lung carcinoma) in the leg and subsequent surgical removal of the tumor (leg amputation), Iloprost (0.2 mg/kg, 1.5 hours before tumor removal) reduced the number of lung metastases by about 50%. But the survival time was only insignificantly lengthened.

SUMMARY OF THE INVENTION

It has now been surprisingly found that Eptaloprost, Cicaprost and combinations of Eptaloprost and Cicaprost with $TXA_2$ antagonist, in contrast with the actions known so far of other prostaoyclins, act selectively antimetastatically, since no action on the growth of the primary tumor can be detected.

The invention thus relates to antimetastatically acting agents containing Eptaloprost, Cicaprost, their addition salts with physiologically compatible bases, their clathrates with cyclodextrins, or one of the above in combination with thromboxane $A_2$ antagonist, further in combination with the usual auxiliary agents and vehicles.

Eptaloprost [(5E)-(16S)-13,14-didehydro-1a,1b-dihomo-16,20-dimethyl-3-oxa-18,18,19,19-tetrahydro-6 a-carbaprostaglandin-$I_2$] and its beta-cyclodextrin clathrate can be produced, for example, according to the following formulation:

17.2 ml of a 50% sodium hydroxide solution and 337 mg of tetrabutyl ammonium hydrogen sulfate are added to a mixture of 6.9 g of 2-[(E)-(1S,5S,6S,7R)-7-(dimethyl-tert--butylsilyloxy)- 6-[(3S,4S)-3-(dimethyl-tert-butylsilyloxy)-4-methyl-nona-1,6-diinyl[-bicyclo[3.3.0]octan-3-ylidene]-ethan-1-ol (W. Skuballa, E. Schillinger, C.-S. Stuerzebecher, M. Vorbruggen, J. Medicinal Chemistry 29, 313 (1986); described here as compound 15a) and 11.5 g of trimethyl-ortho-4 -bromobutyrate and stirred for 16 hours at 22° C. under argon. Then with ice water cooling it is diluted with 20 ml of water and acidified with 10% citric acid solution to pH 5. It is extracted three times with 300 ml of ether each, the organic phase is washed once with 200 ml of brine, dried on magnesium sulfate and concentrated by evaporation in a vacuum. After chromatography of the residue on silica gel with hexane/ether (8+2), 7.6 g of (5E)-(16S)-13,14-didehydro-1a,1b-dihomo-16,20-dimethyl- 3-oxa-18,18,19,19-tetra-dehydro-6a-carbaprostaglandin-$I_2$ -methylester-11,15-bis-(dimethyl-tert-butyl-ether) is obtained as a colorless oil.

IR ($CHCl_3$): 2953, 2925, 2859, 2230, 1730, 1250, 838 $cm^{-1}$.

For silyl ether cleavage, 7.25 g of the above-described bis-silyl ether is stirred for 48 hours at 24° C. with 600 ml of a mixture of acetic acid/water/tetrahydrofuran (65+35+10). Then it is concentrated by evaporation in a vacuum and the residue is chromatographed on silica gel. With ethyl acetate/hexane (3+2), 3.9 g of (5E)-(16S)-13,14 -didehydro-1a,1b-dihomo-16,20-dimethyl-3-oxa-18,18,19,19 -tetradehydro-6a-carbaprostaglandin-$I_2$-methylester is obtained as a colorless oil.

IR ($CHCl_3$): 3400 (broad), 2935, 2865, 2230, 1735 $cm^{-1}$.

For saponification, a solution of 3.66 g of the above-produced methylester is stirred in 35 ml of methanol with 35 ml of an 0.5 molar sodium hydroxide solution for 30 minutes at 24° C. under argon. Then it is diluted with 20 ml of water, acidified with a 20% citric acid to pH 2, extracted 4 times with 100 ml of methylene chloride each, the organic phase is washed once with 50 ml of brine, dried on sodium sulfate and concentrated by evaporation in a vacuum. The residue is chromatographed with ethyl acetate on silica gel. Thus 3.4 g of the title compound is obtained as a colorless oil.

IR ($CHCl_3$): 3400 (broad), 2962, 2940, 2865, 2230, 1722 $cm^{-1}$.

Beta-cyclodextrin clathrate of (5E)-(16S)-13,14 -didehydro-1a,1b-dihomo-16,20-dimethyl-3-oxa-18,18,19,19 -tetra-dehydro-6a-carbaprostaglandin-$I_2$.

41.75 g of beta-cyclodextrin is dissolved in 298 ml of water at 80° C. and a solution of 1.5 g of (5E)-(16S)-13, 14-didehydro-1a,1b-dihomo-16,20-dimethyl-3-oxa-18,18, 19,19-tetradehydro-6a-carbaprostaglandin-$I_2$ in 24 ml of ethanol is instilled in 15 minutes. It is stirred for 4 hours at 60° C. and then allowed to cool overnight with stirring. The precipitated solid is suctioned off, washed with 50 ml of a mixture of water-ethanol (1:1) and dried for 24 hours at 0.1 torr and 25° C. on phosphorus pentoxide. 38 g of free-flowing crystals of the beta-cyclodextrin clathrate of the above-mentioned carbacyclin analog is obtained. The content of carbacyclin analogs in the clathrate is determined by titration and amounts to 3.3%.

Cicaprost and its beta-cyclodextrin clathrate can be produced according to the processes described in EP-PS 119, 949 (CA 1,251,200) and in international laid-open specification WO 87/05294 (U.S. Pat. No. 4,886,788).

As thromboxane receptor antagonist $TXA_2$ all compounds are suitable as they are described, e.g., in: J5 5017-315; U.S. Pat. Nos. 4,472,586; 4,263,207; 4,394,515;

4,282,365: BE 883,713; J5 7093-962; J6 0004-154; EP 43-292; EP 82-646; DE 3,346,047; WO 0400-754: U.S. Pat. Nos. 4,474,804; DE 3,401,986; DE 3,127,343; BE 897-763; EP 74-861; AU 84/25,607; EP 78-668; DE 3,339,019; EP 137,426 and in N. H. Wilson and R. L. Jones in: Advances in Prostaglandin, Thromboxane and Leukotriene Research 14, 420–423 (1985), as well as K. Stegmeier et el. in: Thrombosis Research 35, 379–395 (1984).

There can mentioned, for example:

4-[2-(benzenesulfonamido)-ethyl]-phenoxy acetic acid (BM 13 177) [K. Stegmeier et el. in: Thrombosis Research 35, 379–395, 1984]

[1alpha(Z),2beta,5alpha-(+)-(7)-[5-[[(1,1-biphenyl)-4-yl]methoxy]-2-(4-morpholinyl)-3-oxocyclopentyl]-4-heptanoic acid (AH 23848) (Br. J. Pharmac. (1985), 86, 259)

[1beta,2alpha(5Z),3alpha,4beta]-7-[[2-[(phenylamino)carbonyl]hydrazino]methyl]-7-oxabicyclo[2.2.1]-hept-2-yl]-5-heptenoic acid (SQ to 29.548) (Prostaglandins 29,785 (1985)

4-(4-chlorobenzenesulfonylamino)-ethyl-benzene acetic acid (BM 13 505) (Intern. Conf. Leukotrienes and Prostanoids in Health and Disease, Tel Aviv, Oct. 1985, p. 10).

7-[3-[[[(phenylamino)carbonyl]hydraxonol]methyl]bicyclo-[2.2.1]hept-2-yl]-[1alpha,2beta,(Z),3alpha,4alpha] (EP 045) and 7-[(1S,2S,3S,4R)-3-[1-(3-phenylthioreidoimino)-ethyl]-bicyclo[2.2.1]heptan-2-yl]-5 heptenoic acid (EP 092) [both substances R. A. Armstrong et el. in Br. J. Pharmacol. 84, 595–607, 1985].

dibenzo[b,f]thiepin-3-methanol-5,5-dioxide (L 640035) [C- C. Chan in: Europ. J. Pharmacol. 110 (3), 323–328, 1985].

2,7(1H)-isocluinoline disulfonamides, N7-(3 -chlorophenyl)-N2-[[7-[[(3-chlorophenyl)amino]sulfonyl]-3,4-dihydro-2(1H)-isoquinolinal]sulfonyl]-3,4-dihydro (SKF 88046) [B. M. Weichman et el. in: Prostaglandins Leukotrienes and Medicine 15, 167–175, 1984].

With intravenous infusion of Eptaloprost, Cicaprost, or the above-mentioned combinations, amounts of prostacyclin or prostacyclin analog, for example, of about 1–50 micrograms per patient per day, preferably 12.5 μg/patient/day, are necessary. In oral application, about 125–350 micrograms per patient per day is used.

For the oral application a dose unit contains 25–50 micrograms of prostacyclin or prostacyclin analog, in sustained release formulations 25–250 micrograms, as tablet, coated tablet, capsule, pill, suspension or solution, which can be produced in the usual way with additives and vehicles usual in galenicals.

The thromboxane receptor antagonists are used according to this invention in amounts, which are in the range of the amounts thus far used in human studies [Riess, H. E. Hiller, B. Reihhardt, C. Brauning: in Thrombosis Research 35, 371–378, 1984]. Generally, 100–3000 mg/patient/day, preferably 200–1200 mg/patient/day of BM 13177, or 1–150 mg/patient/day, preferably 2–100 mg/patient/day of AH 23 848 or SQ 29 548, or a biologically equivalent amount of another thromboxane receptor antagonist.

Where the prostacyclins are used along with mixtures of their clathrates and salts, the ratio of one given active agent to another is not important, so long as the biologically equivalent amount of overall active agent is within the quoted ranges.

For the preferred oral application especially tablets, coated tablets, capsules, pills, suspensions or solutions are suitable,.which are mixed in the usual way with additives and vehicles usual in galenicals.

In the combinations amounts by weight of prostacyclin/prostacyclin analogs and of thromboxane receptor antagonist are used, which in common application are greatly reduced in comparison with dosages of individual active ingredients necessary with other indications up to now.

PC/PCA and TXAA are combined into one dose unit or are used separately and simultaneously or sequentially in a weight ratio of substantially about 1:0.1 to 1:100 (e.g., in the same vehicle, a tablet or an oily solution such as a benzyl benzoate/castor oil mixture). Combinations of prostacyclins and $TXA_2$ may be made in a broad range, so long as sufficient prostacyclin is present to achieve a metastatic effect according to the invention. Preferably, the ratio is 1:0.1 to 1:10, more preferably 1:01 to 1:1.

β-Cyclodextrin is preferable as a cyclodextrin for combination with the prostacyclins.

The invention further relates to the use of Eptaloprost, Cicaprost and combinations of $TXA_2$ antagonist and prostacyclin derivatives for the production of a pharmaceutical agent with antimetastatic action. Generally, all malignant human tumors (except leukema-based cancers) produce metastacization, and the invention is applicable thereto.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited above and below, and of corresponding German Application P 39 33 523.2, filed Oct. 5, 1989, are hereby incorporated by refrence.

EXAMPLE

The cell line R 3327 MAT-LU is used in the following tests. This cell line is discussed in the review article of J. T. Isaacs (Current Concepts and Approaches to the Study of Prostate Cancer 513–576, 1987, Alan R. Liss, Inc., Animal Model Systems), on page 533. The researchers and laboratory indicated as first isolating this MAT-Lu subline were D. W. Lanzan, W. D. W. Heston, D. Kadmon and W. R. Fair (Division of Urology, Dept. of Surgery, Washington University School of Medicine, St. Louis). Moreover, in the above article, animal strains are described in which this sunline develops, and detailed growth characteristics of this cell line are indicated. D. W. Lazan et al. describe in Cancer Research 42,1390 (1982), how an individual cell suspension of R 3327 MAT-Lu tumor cells is prepared with a freshly excised side tumor from an individual rat.

The R 3327 MAT-Lu, obtained by Dr. Isaacs of John Hopkins University, is fast-growing, endocrine-independent and exhibits no measurable steroid receptors. The metastasizing rate is 100%. The survival time of animals after s.c. implantation is about 35 days. An arrangement with s.c. implantation without removal of the primary tumor was selected to detect an antimetastatic action of prostacyclin derivatives or of the combination products of $TXA_2$ antagonist and prostacyclins.

1. The tumor is removed under aseptic conditions from the donor animal about 4 weeks after implantation. In MEM 199 (minimum essential medium, standardized medium of Gibco company, UK) the tumor is freed of necrotic portions and cut in pieces about 2 mm edge length. One tumor piece each is implanted subcutaneously in adult, male Cop rats (OLAC, England). The animals are randomized to 4 groups of 10 animals each. Already on the previous day, Alzet minipumps were implanted s.c. in the animals. Group 1: solvent; group 2: Iloprost (300 ng/kg/min); group 3: Eptaloprost (100 ng/kg/min). On day 16 the pumps are replaced.

The tumors are measured once a week with a sliding caliper. The tumor surface is calculated as the product of the greatest diameter and of the diameter perpendicular to it. At the end of the test the animals are killed by decapitation. The level of active ingredients in the blood is determined. The lungs are dissected, fixed in Bouin solution for 24 hours and then preserved in alcohol. The number of lung metastases is determined by counting. This is made easier because metastases cannot be stained by Bouin. Further, a classification into "large" and "small" metastases is performed.

2. Action of Iloprost and Eptaloprost On R 3327 MAT-LU PC

In the selected test arrangement (s.c implantation of the tumor, no removal of the primary tumor), the requirements placed on the antimetastatic action are classified as very high, since the primary tumor continuously produces metastases.

At the end of the test the body weight was not significantly reduced under therapy with prostacyclins

|  | Body Weight (g) | Tumor Surface (mm²) |
| --- | --- | --- |
| Control | 315 ± 28 | 1966 ± 791 |
| Iloprost | 282 ± 43 | 1658 ± 485 |
| Eptaloprost | 281 ± 43 | 1928 ± 691 |

The tumor growth took place very progressively starting from about day 12 after implantation (FIG. 1). A specific inhibitor of metastasizing should have no effect on the growth of the primary tumor. With Iloprost and Eptaloprost there is also no difference in the growth of the primary tumor in comparison with the control.

The evaluation of the lung metastases of this PC metastasizing only in the lung provides solely information on the antimetastatic potential. The located metastases vary in their size from less than 1 mm in diameter to about 3 mm. A division into "small" and "large" metastases can be made without the occurrence of many borderline cases.

With Iloprost no reduction of the total number of lung metastases can be detected in this model. However, Eptaloprost results in significant and marked inhibition of the total number of metastases (FIG. 2). In a division into "large" and "small" metastases for Iloprost there is a trend to the reduction of the number of "large" metastases (FIG. 3), while the number of "small" metastases in comparison with the control has a tendency to increase (FIG. 4). Also the marked effect on the metastasis number with Eptaloprost is more strongly pronounced with "large" metastases than with "small" metastases.

3. In a second experiment with the same test arrangement as under 2., Eptaloprost is applied in doses of 0.1 to 0.5 mg/kg daily orally from the day of tumor implantation to the end of the test. Again there is no action on the primary tumor. While in the 0.1 mg/kg dose, no effect on the number of lung metastases can be detected, Eptaloprost in the higher dose of 0.5 mg/kg of body weight results in a significant (p less than 0.05, Dunnett test) reduction of the metastasis number (FIG. 5).

Figure 1:
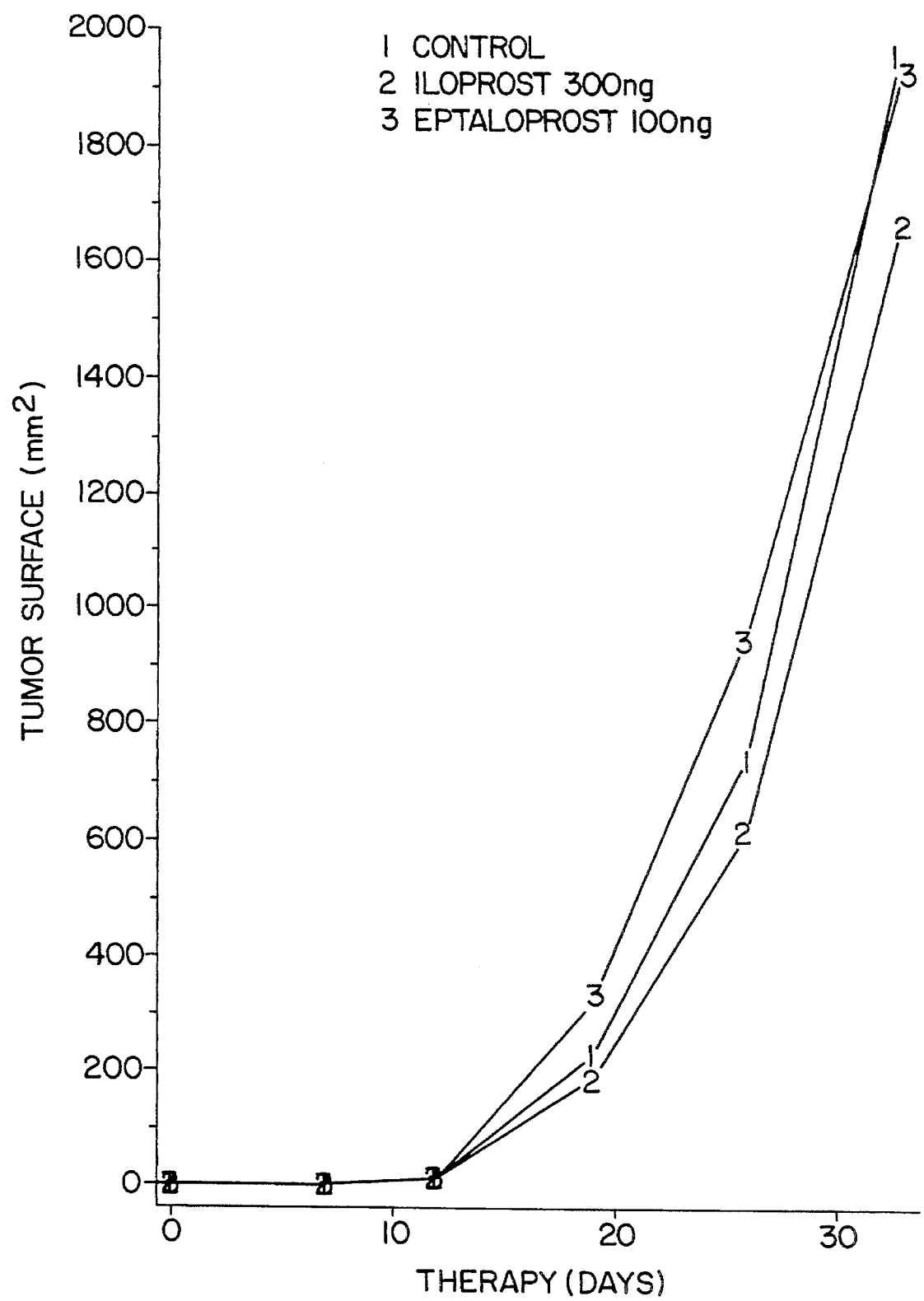
FIG. 1: Action of Iloprost and Eptaloprost on the growth of R 3327 MAT-Lu (primary tumor).
Figure 2:
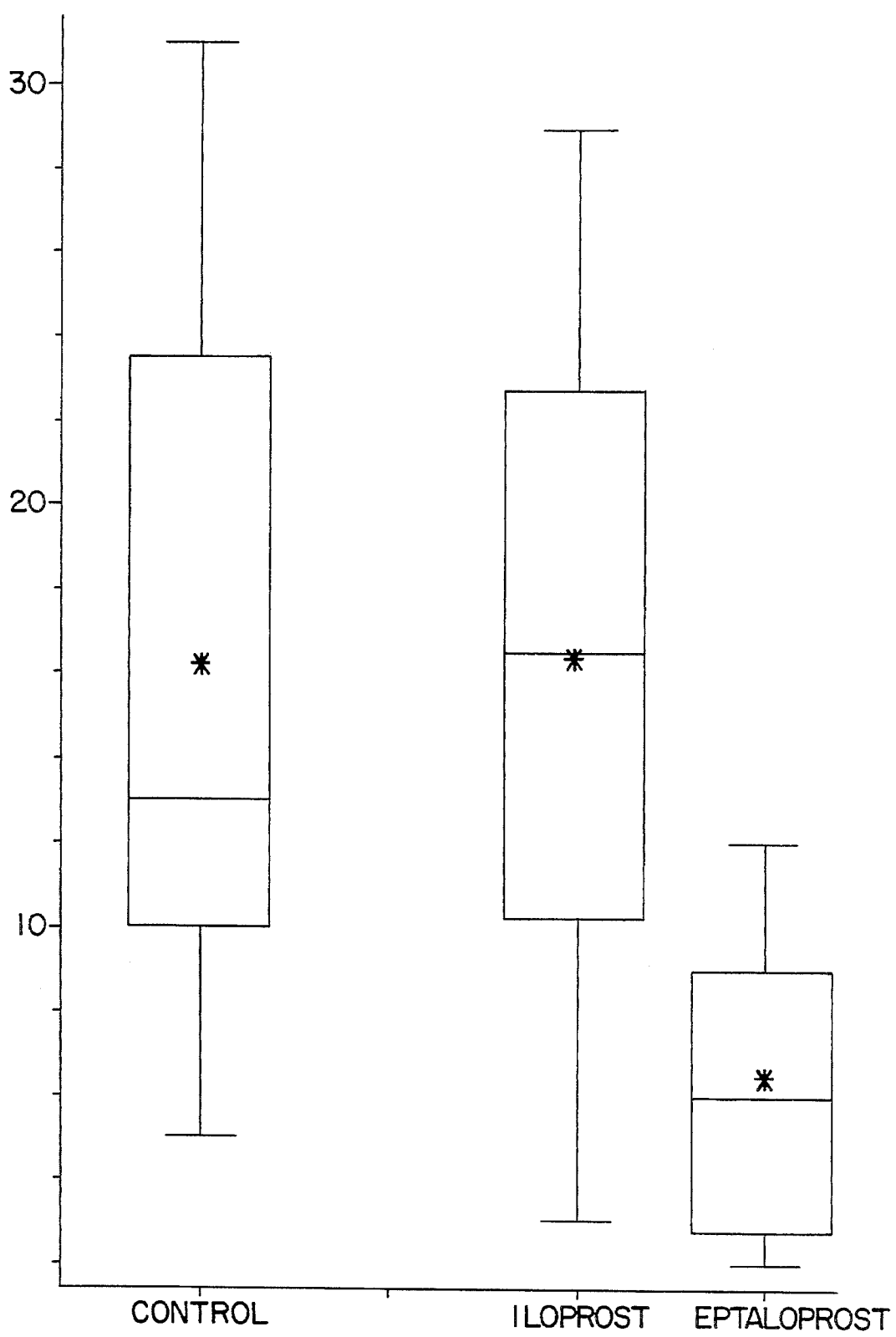
FIG. 2: Action of Iloprost and Eptaloprost on the total number of lung metastases.
Figure 3:
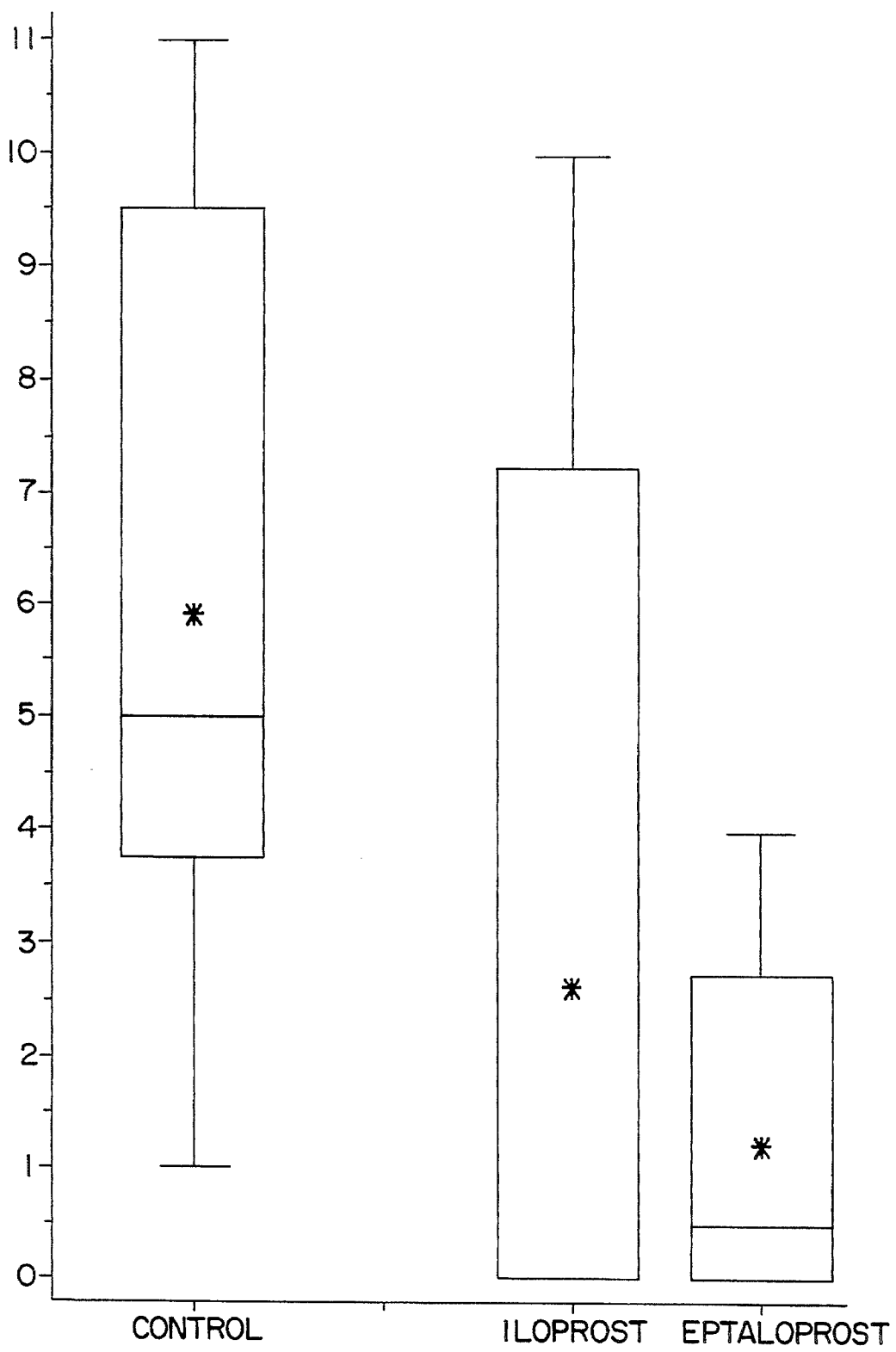
FIG. 3: Action of Iloprost and Eptaloprost on the number of "large" lung metastases.
Figure 4:
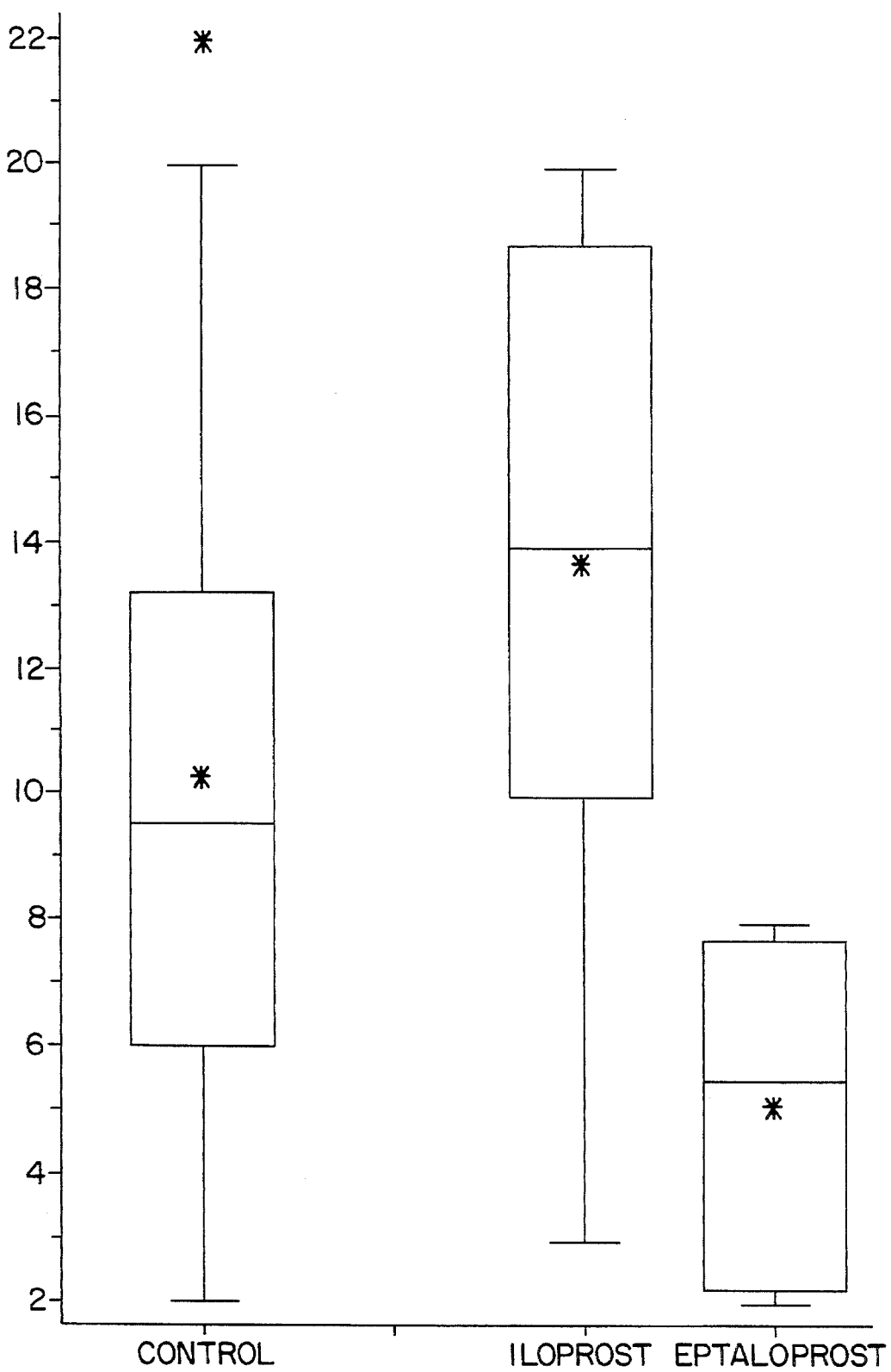
FIG. 4: Action of Iloprost and Eptaloprost on the number of "small" lung metastases.
Figure 5:
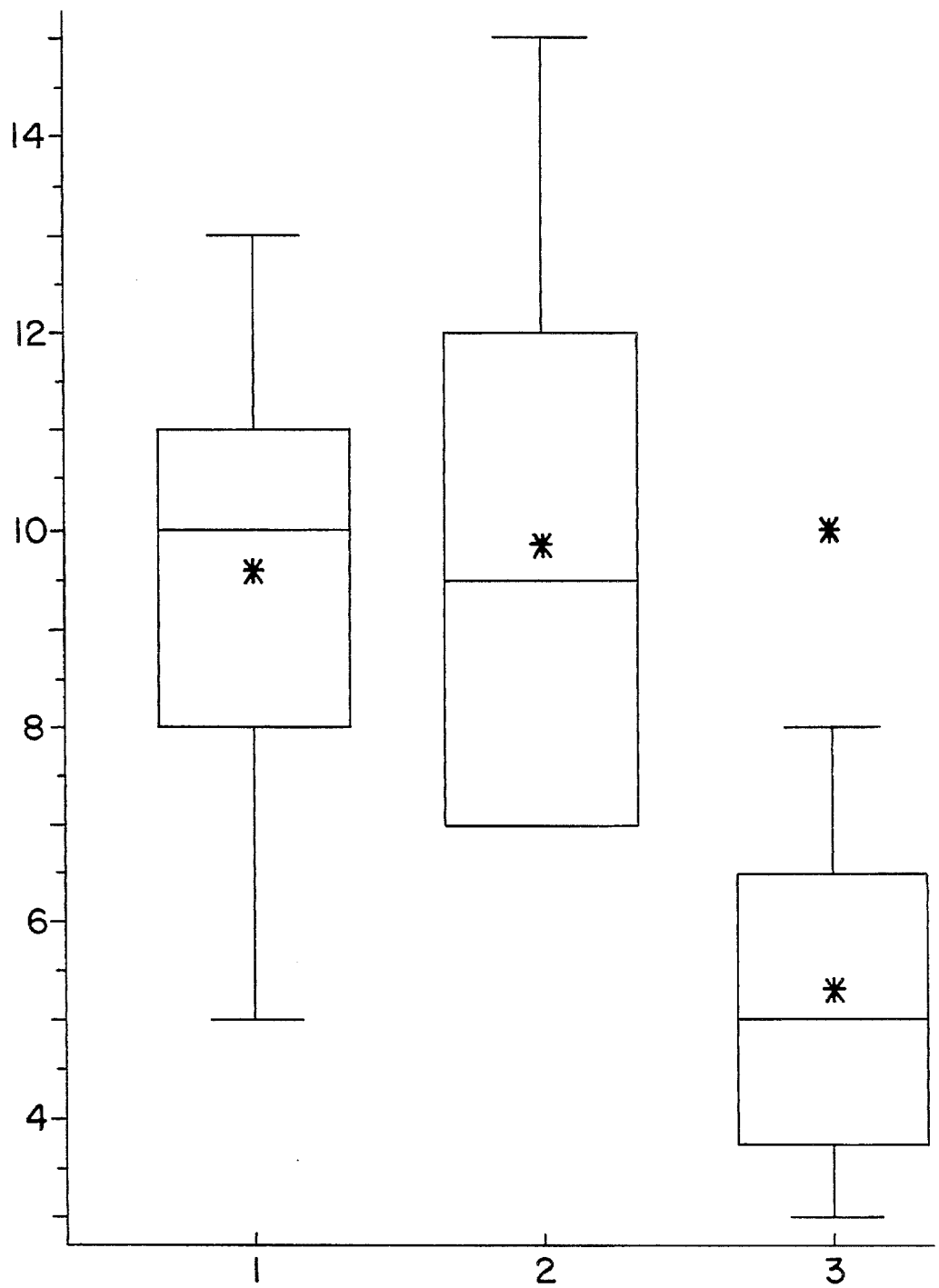
FIG. 5: Action of Eptaloprost in various dose amounts on the number of lung metastases.

What is claimed is:

1. A method of inhibiting, in a host, metastases of a malignant tumor sensitive to treatment with Eptaloprost or Cicaprost, comprising administering to said host an effective amount of Eptaloprost or a Cicaprost, an addition salt of Eptaloprost or Cicaprost with a physiologically compatible base, a cyclodextrin clathrate, or a mixture thereof.

2. A method of claim 1, comprising administering Eptaloprost.

3. A method of claim 1, comprising administering an Eptaloprost cyclodextrin clathrate.

4. A method of claim 1, comprising administering Cicaprost.

5. A method of claim 1, comprising administering a Cicaprost cyclodextrin clathrate.

6. A method of claim 1, comprising administering Eptaloprost, Cicaprost, or an addition salt thereof in combination with an effective amount of thromboxane receptor antagonist.

7. A method of inhibiting, in a host, metastases of a prostatic cancer, comprising administering to said host an effective amount of Eptaloprost, Cicaprost, an addition salt of Eptaloprost or Cicaprost with a physiologically compatible base, a cyclodextrin clathrate, or a mixture thereof.

8. A method of inhibiting, in a host, metastases of a mammary tumor, comprising administering to said host an effective amount of Eptaloprost, Cicaprost, an addition salt of Eptaloprost or Cicaprost with a physiologically compatible base, a cyclodextrin clathrate, or a mixture thereof.

9. A method of inhibiting, in a host, metastasis of a carcinoma having metastatic activity, comprising administering to said host an effective amount of Eptaloprost, Cicaprost, an addition salt of Eptaloprost or Cicaprost with a physiologically compatible base, a Cyclodextrin clathrate, or a mixture thereof.

* * * * *